United States Patent [19]

Jamner

[11] Patent Number: 5,235,966
[45] Date of Patent: Aug. 17, 1993

[54] ENDOSCOPIC RETRACTOR

[76] Inventor: Jay Jamner, 36 Lismore La., Greenwich, Conn. 06831

[21] Appl. No.: 779,361

[22] Filed: Oct. 17, 1991

[51] Int. Cl.⁵ .............................................. A61B 17/02
[52] U.S. Cl. ...................... 128/20; 606/198; 606/207; 606/208
[58] Field of Search ................ 128/20, 3, 4; 606/205, 606/206, 207, 208, 191, 198, 170; D24/133, 135, 143

[56] References Cited

U.S. PATENT DOCUMENTS

| | | | |
|---|---|---|---|
| 832,201 | 10/1906 | Kistler | 606/198 X |
| 1,331,737 | 2/1920 | Ylisto | 606/198 |
| 3,266,494 | 8/1966 | Brownrigg et al. | 606/206 |
| 3,667,474 | 6/1972 | Lapkin et al. | 606/198 |
| 4,591,355 | 5/1986 | Hilse | 604/159 |
| 4,909,789 | 3/1990 | Taguchi et al. | 606/198 X |
| 4,950,273 | 8/1990 | Briggs | 606/205 X |
| 4,997,432 | 3/1991 | Keller | 606/206 X |
| 5,035,248 | 7/1991 | Zinnecker | 606/205 X |
| 5,052,402 | 10/1991 | Bencini et al. | 606/206 X |
| 5,104,383 | 4/1992 | Shichman | 604/167 |

OTHER PUBLICATIONS

Le Qvinziéme Livre, 1840, pp. 484–486, and p. 788.

Primary Examiner—Richard J. Apley
Assistant Examiner—Karen Jalbert
Attorney, Agent, or Firm—Rosen, Dainow & Jacobs

[57] ABSTRACT

The invention relates to an endoscopic retractor suitable for use in laporoscopic surgery to retract, separate, and expose different tissues, organs and viscera, in manner similar to conventional open surgery retractors.

12 Claims, 3 Drawing Sheets

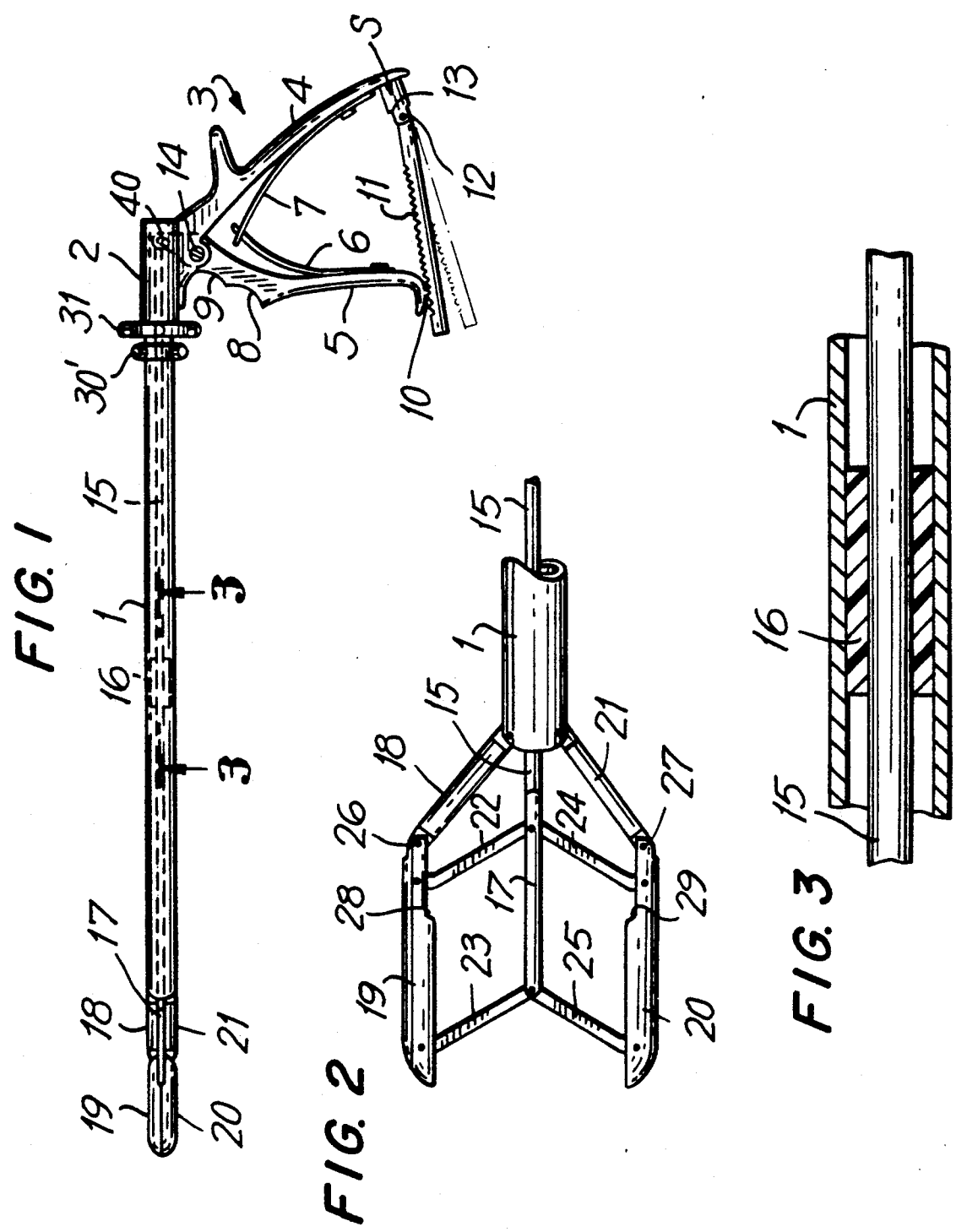

ENDOSCOPIC RETRACTOR

TECHNICAL FIELD

The present invention relates to an endoscopic retractor suitable for use in surgeries where minimal invasive surgical procedures are desired. The endoscopic retractor embodied in the present invention is used in laparoscopic surgery to retract, separate, and expose different tissues, organs and viscera, in a way similar to conventional open surgery retractors.

As described in greater detail hereinafter, the retractor comprises an elongated hollow tubular shaft having at one end thereof, an expandable segmented tip actuated by a substantially rigid connecting rod extending through said tubular section to the other end thereof to hand operated actuating drive means that is used to expand or close the expandable segmented tip members.

The retractor is inserted into an abdominal cavity with the expandable tip in a closed, i.e. not expanded, position. By use of the hand operated drive means, the surgeon causes the tip to expand the desired amount in place, for example, between organs. The result is that the endoscopic device acts as an intra-corporeal retractor.

PRIOR ART

U.S. Pat. Nos. 832,201 and 1,267,066 relate to dilators that are expandable, however, the articles described in these references do not contain the many elements of the present invention.

U.S. Pat. Nos. 1,347,651, 1,361,649 and 1,879,339 disclose tonsillotomes, each of which contain a handle that allows the manipulation of the surgical instrument by hand; however, the overall structures of these articles are totally different from the retractor of the present invention.

U.S. Pat. No. 1,392,085 discloses a syringe that contains several dilating fingers which are designed to move outwardly when the syringe is in use. This article also does not contain the elements of the present invention.

U.S. Pat. No. 3,667,474 discloses a dilator for performing mitral and tricuspidal commisurotomy per atrium cordis and has a working head with jaws, a flexible rod and a handle to dilate the head. The structure of the mechanism that directs and controls the opening and closing of the head of the present invention is different from that disclosed in the reference. As noted hereinafter, the retractor of the present invention can be rotated 360° to provide optimum positioning with minimum instrument movement. Further, a dual rotating lock system permits the retractor of the present invention to be locked in place at any point of the rotation. The reference does not teach these elements.

U.S. Pat. No. 4,909,789 discloses observation assisting forceps adapted to assist the observation with an endoscope by moving an internal organ to a place easy to observe by projecting linear or rod shaped members expanding out of the sheath. Although the article in the aforementioned patent is designed to be used with an endoscope, the structure of the actual article is different from the retractor of the present invention.

BRIEF DESCRIPTION OF THE DRAWINGS

FIG. 1 is a side cross sectional view of the retractor of the present invention.

FIG. 2 is a side cross sectional view of the retractor blades fully expanded.

FIG. 3 is a cross sectional view of a section of the hollow tubular shaft containing the actuating rod therein and the inner seal that prevents loss of fluid through the surgical procedure.

DETAILED DESCRIPTION OF THE PREFERRED EMBODIMENT

Figure 4:
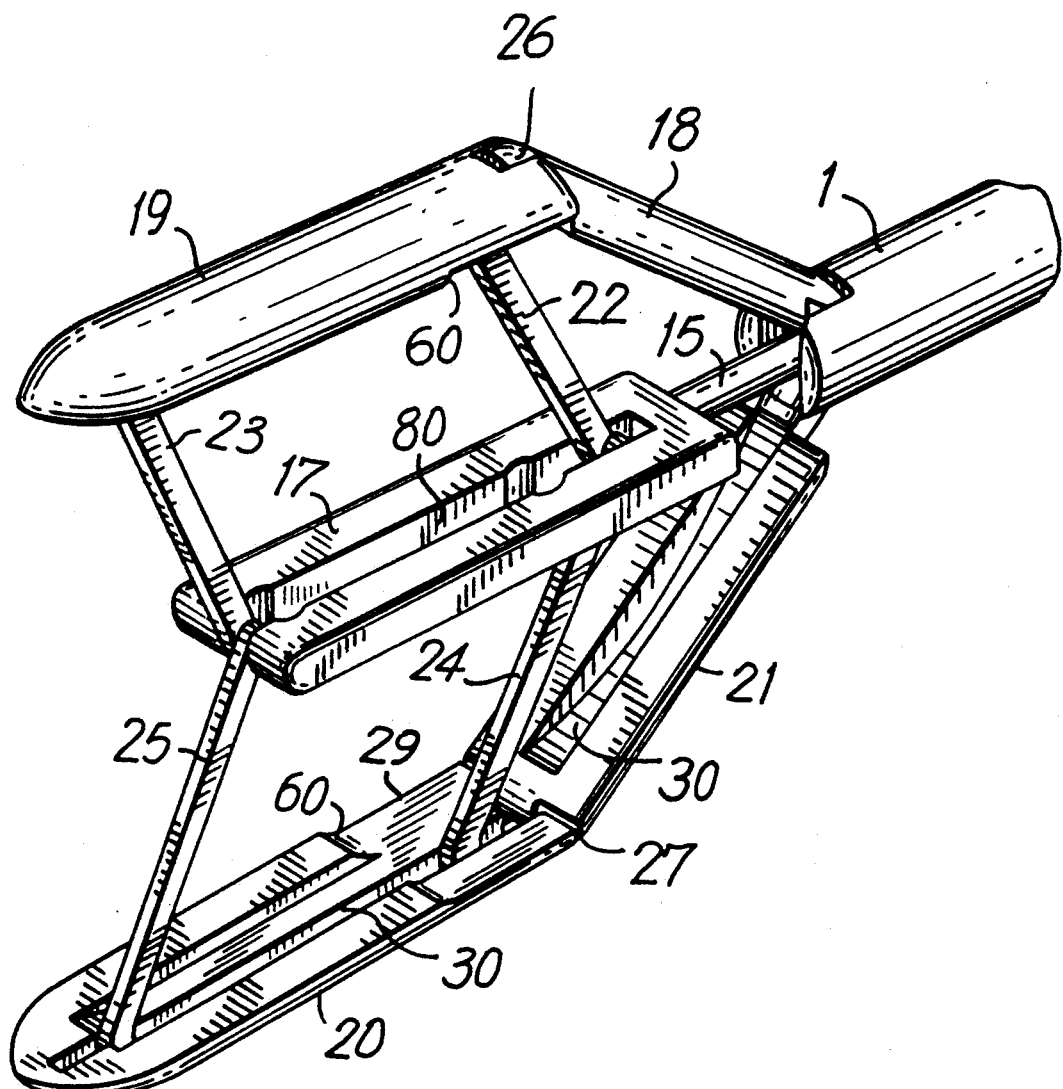
FIG. 4 is a perspective view of the retractor blades fully expanded.

As shown in FIG. 1 the endoscopic retractor of the present invention comprises a hollow tubular shaft 1 of relatively small diameter that is attached at one end to a breech section 2 which has affixed to its underside, handle grip 3 comprising fixed handle 4 and movable trigger 5. While it is preferable that shaft 1 be circular in cross section so as to occupy a minimal area, the shaft can be square, rectangular or any other cross section that is desired or convenient. The position of trigger 5 with respect to handle 4 is maintained in place at rest as a result of cooperating leaf springs 6 and 7. Along the forward edge of movable trigger 5 toward the area of breech 2 are two indentations 8 and 9 which conform to and may if desired be used to receive the fingers of the surgeon while using the instrument. At the lower portion of movable trigger 5, is pawl 10 which works in combination with the teeth found along the upper surface of ratchet bar 11 to hold movable trigger 5 in place at a desired location during the surgical procedure. Ratchet bar 11 is pivotally mounted at 12 to one end of a bracket or support bar 13 extending out from the interior side of fixed handle 4 beneath leaf spring 7. An end portion of ratchet bar 11 that extends into the interior of bar 13 beyond the pivot 12 bears on a spring S, the tension of which forces the teeth along ratchet bar 11 into engaging contact with pawl 10. To return movable trigger 5 to its normal or rest position it is only necessary to remove the upward tension that spring S impresses on ratchet bar 11, whereupon, trigger 5 snaps back to its normal or rest position.

When desired, ratchet bar 11 can be swung down and out of engagement with pawl 10 as shown by the phantom line position, and trigger 5 will assume the normal or rest starting position.

Movable trigger 5 is secured to fixed handle 4 at pivot hinge 14 and an end portion extends up into the interior of breech 2. Within the breech, at the upper portion of trigger 5 is a lug or arm 40 which privotally engages actuator rod 15 for movement between the open and closed positions of segmented tip members 18, 19, 20 and 21. Thus, for example, when movable trigger 5 is squeezed along ratchet bar 11 toward fixed handle 4, actuating rod 15 is advanced in a direction opposite to the direction that movable trigger 5 is moving and thereupon the segmented tip members flare open.

Actuating rod 15 extends through the interior of hollow shaft 1 concurrently through an impermeable gas tight seal 16 through the opposite end of shaft 1 where it is affixed to pivot support means 17, that possesses a width (lateral) substantially identical to the diameter of tubular shaft 1. As shown in FIG. 1, the expandable segmented tip comprising retractor blades 19 and 20 and connecting arms 18 and 21 are positioned atop and beneath respectively the pivot support plate means 17. For example, as shown in FIG. 1, retractor blade 20 and connecting arm 21 are connected on the underside of rectangular pivot support plate means 17. Since the shaft and tip are rotatable, the relative positions of the tip elements can be reversed.

Elements 18, 19, 20 and 21 are preferably circular in cross section and possess radii substantially identical to that of tubular shaft 1.

FIG. 1 depicts the retractor in the closed state. Retractor blades 19 and 20, when in the closed state, possess a stream line or bullet shaped tip which permits a nontraumatic entry of the device into the body.

It has been determined that the endoscopic retractor of the present invention can be used in purely diagnostic laparoscopy or therapeutic laparoscopic operations. The retractor with the blades closed as depicted in FIG. 1 is inserted into the abdominal cavity through a cannula. At the appropriate location in the abdomen, the surgeon opens blades 19 and 20 by squeezing movable trigger 5 toward fixed handle 4. As the surgeon squeezes movable handle 5, pawl 10 moves from tooth to tooth along ratchet bar 11 and this action spreads or flares retractor blades 19 and 20 that expand parallel to each other, and causes connecting arms 18 and 21 to assume an increasing angle from the horizontal plane as retractor blades 19 and 20 move further apart.

At any time the surgeon stops advancing the movable trigger 5, pawl 10 is engaged and held in place by the tooth in ratchet bar 11 which it is engaging, thereby controlling the extent (i.e. the distance) to which retractor blades 19 and 20 are separated from each other. By advancing movable trigger 5 toward handle 4, actuating rod 15 is advanced forward and retractor blades 19 and 20 are moved further apart.

When the surgeon has squeezed movable trigger 5 along ratchet bar 11 to the last notch, the tip of the device assumes a position as depicted in FIG. 2. FIG. 2 shows hollow tubular shaft 1 in place and shows actuating rod 15 affixed to pivot support plate element 17. Pivotally attached within a slotted opening along the longitudinal axis of plate 17 are coupler links 22 and 23 and 24 and 25 which are attached to retractor blades 19 and 20 respectively. The interior surfaces of retractor blades 19 and 20 contain a groove 30 cut along each of the longitudinal center line of blades 19 and 20 in order to accommodate coupler links 22, 23, 24 and 25 when retractor blades 19 and 20 are in the closed position.

Connecting arms 18 and 21 are pivotally attached at the end of tubular shaft 1 and pivotally attached at the other end to retractor blades 19 and 20 respectively via articulated joints 26 and 27. Longitudinal sections of retractor blades 19 and 20 along their horizontal axes have been removed at locations 28 and 29 respectively to provide a slot for rectangular pivot support plate 17 to rest in when retractor blades 19 and 20 are closed.

The ratchet and pawl arrangement present in the handle provides, the surgeon with the ability to separate the retractor blades at small increments as needed or desired.

In addition, adjacent to breech 2 is an adjustment finger nut 30' which is secured, to tubular shaft 1 so that when adjustment finger nut 30' is rotated, the entire tubular shaft along with retractor blades 19 and 20 and the other elements present at the tip of the device are correspondingly rotated. Thus, the entire shaft, retractor blades etc. can be rotated 360° to provide optimum positioning with minimum instrument movement.

Next to adjustment finger nut 30', is a tightening finger nut 31 which secures and fixes the shaft and retractor blades in place when tightened against breech 2. This rotating lock system permits the blades to be locked in place at any point of the rotation.

FIG. 3 is a cross sectional view taken along the lines 3—3 of FIG. 1 and depicts the inner seal 16 within tubular shaft 1 showing actuating rod 15 extending through the center thereof. The seal in most instances is about 4 cm long, however, its length is not critical as it need only be of a length sufficient to prevent the passage of a gas such as $CO_2$ used during surgeries of this type. The seal is made of any material that will provide an impervious barrier to any gas that is used during the surgery. Polytetrafluoroethylene is one such suitable material. In use, the seal prevents the loss of gas during pneumoperitoneum.

FIG. 4 is a perspective view of the segmented retractor tip that is in the expanded state. Slot 80 through plate 17 is depicted and coupler links 22 and 23 and 24 and 25 are pivotally connected to plate 17. FIG. 4 also depicts groove 30 cut along the center of the longitudinal axes of elements 20 and 21 adapted to accommodate coupler links 24 and 25. An area 29 of retractor blade 20 has been chamfered at location 60 and the area so removed from retractor blade 20 is adapted to receive pivot support plate 17.

Figure 5:
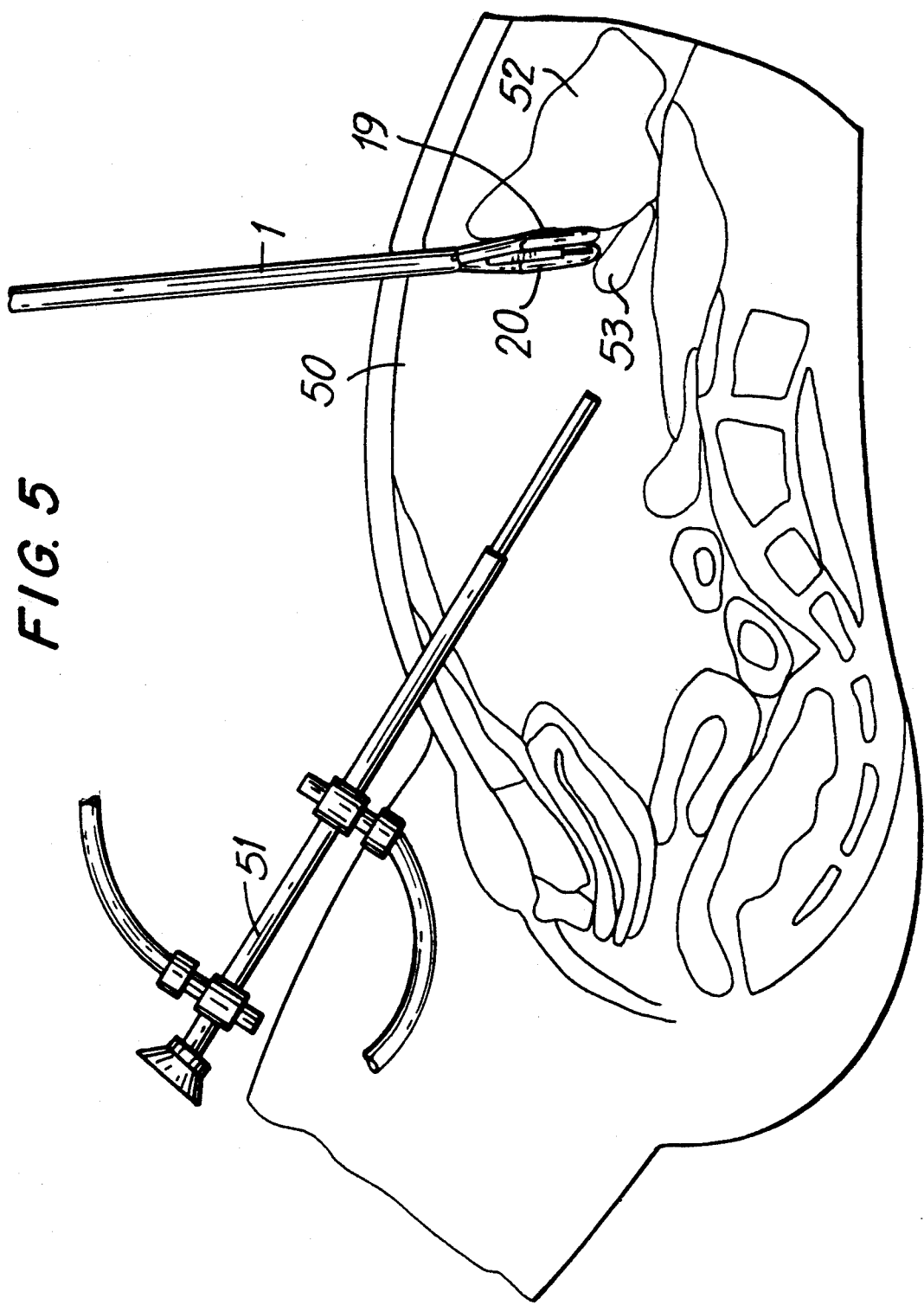
FIG. 5 is a cross sectional view of the torso through the medial sagittal plane.

FIG. 5 is a cross sectional view of a human torso through the medial sagittal plane depicting the endoscopic retractor 1 inserted into the abdominal cavity of torso 50 with expanded retractor blades 19 and 20. The laparoscope 51 is in place for use during surgery. Endoscopic retractor 1 is inserted into the abdominal cavity and is in place in the expanded position thereby separating the liver 52 from gall bladder 53. Using laparoscope 51 in combination with retractor 1, the surgery can be completed. The smooth surface of the tip allows the endoscopic retractor to be inserted into the body with substantially less risk of traumatizing organs, etc. within the body than with previous endoscopic devices.

Preferably, the retractor of the present invention is made from stainless steel and is made in two sizes comprising 5 mm or 10 mm diameters. These diameters are preferable because they are designed to fit through the standard corresponding cannulae used during operations. Obviously the retractor can be made in any size that is convenient depending upon the need.

The retractor, if desired, also can be made from other materials including thermoplastic or thermosetting materials if, for example, it is desired to make the retractor as a disposable item.

As noted above, the endoscopic retractor of the present invention can be used in purely diagnostic laparoscopy. It has been used in mobilization and retraction of the liver; allowing visualization of the majority of this organ. This is particularly important in the identification and biopsy of certain types of very small lesions. One can differentiate these tumorous lesions from other pathologies (small cysts or hemangiomas).

It can be utilized for complete exposure of the gastroesophageal junction; a very useful maneuver for truncal and selective vagotomies. Further it is useful for mobilization and broad exposure of the distal third of the esophagus utilizing the 10 mm retractor to retract the left lobe of the liver upwards, and the 5 mm retractor to retract downwards and to the left of the gastric body. This provides good exposure of the lower curvature of the stomach and visualization of the anterior branch of the nerve of Latarjet, a fundamental maneuver for selective vagotomies.

Retraction and exposure of the left diaphragm and sternal surface of the spleen can also be performed. This facilitates the visualization of this organ and would eventually be useful for biopsies and staging of some lesions, especially lymphomas.

The device allows wide and adequate exposure of parietal adhesions and herniary orifices of the abdomen, (including but not limited to inguinal, crural ring and even esophageal hiatus).

During therapeutic laparoscopic operations the device can be used in the following:

1. Tenting of the abdominal wall facilitating the insertion of trocars in difficult cases, and avoiding visceral lesions or lesions of the great vessels.

2. Laparoscopic cholecystectomy. Exposure and elevation of the gall bladder for better dissection, and visualization of the structures in the triangle of Calot (cystic duct, cystic artery, including the right hepatic and the common bile duct). The exposure and canalization of the cystic duct for intra-operative cholangiography is facilitated. Inspection of the gall bladder bed after removal of the gall bladder and ability to look for and coagulate small bleeders. Retraction and mobilization of the duodenum. Better identification of the common bile duct.

3. Pelvic lymphadenectomies for staging of carcinomas of the bladder and prostate. Excellent exposure of the urinary bladder when retracted towards the midline.

4. Appendectomies.

5. Exposure of structures and organs of the female pelvis in gynecological surgery. The retraction upwards and forwards of the uterus allows wide exposure of the bottom of the Sac of Douglas (particularly important in pelvic endometriosis).

6. Hysterectomy.
7. Tubal ligation.
8. Thoracoscopy.
9. Endometriosis.
10. Adhesiolysis
11. Bowel Surgery The advantages and uses of the present invention are illustrated above and additional operations and advantages will be readily apparent without further explanation. The instrument may be made in any desired size, and as noted above, from any material suitable for the use described, and the proportions of the parts may be varied by one skilled in the art without departing from the spirit of the invention and the scope of the claims.

What I claim and desire to protect by Letters Patent is:

1. An endoscopic retractor comprising:
    a hollow shaft, secured at a first end thereof to hand actuating means;
    and having a second end to which is pivotally attached a segmented expandable tip,
    said tip comprising a pair of matching retractor blades positioned directly opposite each other, each attached to a corresponding connecting arm via an articulating joint, also directly opposite one another, said retractor blades and said connecting arms being aligned along their respective longitudinal axes and each having a circular periphery with approximately the same radius as one another and said hollow shaft;
    a substantially rigid actuating rod which at its first end engages and is moved by said hand actuating means, and which extends through the interior of said shaft through gas impermeable seal means to a second end that is attached to a pivot support plate,
    said pivot support plate being positioned between said matching pairs of retractor blades and connecting arms having a width substantially identical to the width of said shaft and having a plurality of coupler linkages pivotally attached thereto at one end of each said linkages, the other end of each said linkages being slideably engaged in a recessed slot in the surfaces of said retractor blades that face each other,
    said retractor blades and connecting arms moving with respect to each other as a result of movement of said hand actuating means that actuates said actuating rod and moves said pivot plate.

2. The endoscopic retractor defined in claim 1 wherein said hand actuating means comprise a breech member which has affixed to its underside a handle grip suitable for actuating said actuating rod.

3. The endoscopic retractor defined in claim 2 wherein said handle grip comprises a fixed handle and a movable trigger.

4. The endoscopic retractor defined in claim 3 wherein said handle grip comprises a pair of cooperating leaf springs to retain said movable trigger in a rest position.

5. The endoscopic retractor defined in claim 4 wherein said movable trigger has a pawl at the lower end thereof and said fixed handle has extending therefrom toward said movable trigger, a ratchet bar with a plurality of teeth, said movable trigger being held in place as a result of said pawl engaging one of said teeth on said ratchet bar.

6. The endoscopic retractor defined in claim 5 wherein spring means retains said tooth on said ratchet bar in engaging relationship with said pawl.

7. The endoscopic retractor defined in claim 6 wherein said ratchet bar can be disengaged from said pawl to allow said movable trigger to resume a rest position.

8. The endoscopic retractor defined in claim 7 wherein said seal comprises polytetrafluoroethylene.

9. The endoscopic retractor defined in claim 8 that contains adjustment means to rotate said shaft and tip relative to said fixed handle, and lock means to secure said shaft and tip in place.

10. The endoscopic retractor defined in claim 9 wherein said shaft is circular and is 10 mm in diameter.

11. The endoscopic retractor defined in claim 9 wherein said shaft is circular and is 5 mm in diameter.

12. The endoscopic retractor defined in claim 8 wherein said seal has a length of about 4 cm.

* * * * *